(12) United States Patent
Rokde et al.

(10) Patent No.: US 10,603,465 B2
(45) Date of Patent: Mar. 31, 2020

(54) ILLUMINATED GASTRIC TUBES AND METHODS OF USE

(71) Applicant: Covidien LP, Mansfield, MA (US)

(72) Inventors: Rajat Rokde, Pune (IN); Syed Ahmed Mushtaque, Andhra Pradesh (IN); Jeetendra Bharadwaj, Lafayette, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 16/252,758

(22) Filed: Jan. 21, 2019

(65) Prior Publication Data

US 2019/0151131 A1 May 23, 2019

Related U.S. Application Data

(62) Division of application No. 14/276,269, filed on May 13, 2014, now Pat. No. 10,182,933.

(51) Int. Cl.
*A61M 25/00* (2006.01)
*A61B 17/32* (2006.01)
(Continued)

(52) U.S. Cl.
CPC ...... *A61M 25/0082* (2013.01); *A61M 25/007* (2013.01); *A61B 1/0676* (2013.01);
(Continued)

(58) Field of Classification Search
CPC ............ A61M 25/0069; A61M 25/007; A61M 25/0082; A61M 25/04; A61M 2025/0096;
(Continued)

(56) References Cited

U.S. PATENT DOCUMENTS 3,227,154 A 1/1966 Cook
4,328,805 A 5/1982 Akopov et al.
(Continued)

FOREIGN PATENT DOCUMENTS

CN 201365906 Y 12/2009
CN 102626536 A 8/2012
(Continued)

OTHER PUBLICATIONS

European Search Report, dated Mar. 19, 2015, corresponding to European Application No. 14192226.0; 7 pages.
(Continued)

*Primary Examiner* — Shefali D Patel
(74) *Attorney, Agent, or Firm* — Carter, DeLuca & Farrell, LLP (57) ABSTRACT

A gastric tube for use in a bariatric surgical procedure includes an elongate tube and an anchor. The elongate tube has a proximal end portion and a distal end portion and defines a lumen along a length thereof. The proximal end portion defines an opening in communication with the lumen. The elongate tube includes a blunt tip, a light source, and an outer surface. The blunt tip is formed on the distal end portion and is at least partially transparent. The light source is in communication with the blunt tip for illuminating at least the blunt tip. The outer surface extends between the proximal and distal end portions and defines a side opening in communication with the lumen.

19 Claims, 6 Drawing Sheets

(51) Int. Cl.
  *A61B 1/06* (2006.01)
  *A61F 5/00* (2006.01)
  *A61M 3/02* (2006.01)
  *A61B 17/00* (2006.01)

(52) U.S. Cl.
  CPC .......... *A61B 17/320016* (2013.01); *A61B 2017/00818* (2013.01); *A61B 2017/320044* (2013.01); *A61F 5/003* (2013.01); *A61F 5/0083* (2013.01); *A61F 5/0089* (2013.01); *A61M 3/0283* (2013.01); *A61M 25/0069* (2013.01); *A61M 2210/1042* (2013.01); *A61M 2210/1053* (2013.01)

(58) Field of Classification Search
  CPC .. A61M 2210/1042; A61M 2210/1053; A61M 2210/1057; A61M 2210/106; A61M 2210/1064
  See application file for complete search history.

(56) References Cited

U.S. PATENT DOCUMENTS

| | | | |
|---|---|---|---|
| 4,403,604 | A | 9/1983 | Wilkinson et al. |
| 5,246,456 | A | 9/1993 | Wilkinson |
| 5,297,536 | A | 3/1994 | Wilk |
| 5,382,231 | A * | 1/1995 | Shlain ............ A61B 17/0218 128/898 |
| 5,401,241 | A | 3/1995 | Delany |
| 5,458,131 | A | 10/1995 | Wilk |
| 5,465,709 | A | 11/1995 | Dickie et al. |
| 5,718,666 | A | 2/1998 | Alarcon |
| 7,153,131 | B2 | 12/2006 | Crohn |
| 8,092,378 | B2 | 1/2012 | Roth et al. |
| 8,147,502 | B2 | 4/2012 | Albrecht et al. |
| 8,192,448 | B2 | 6/2012 | Bessler et al. |
| 8,454,503 | B2 | 6/2013 | Roth et al. |
| 8,663,149 | B2 | 3/2014 | Gagner et al. |
| 2002/0091395 | A1 | 7/2002 | Gabbay |
| 2003/0093088 | A1 * | 5/2003 | Long ............ A61B 1/0008 606/129 |
| 2004/0006351 | A1 | 1/2004 | Gannoe et al. |
| 2004/0092974 | A1 | 5/2004 | Gannoe et al. |
| 2005/0119674 | A1 | 6/2005 | Gingras |
| 2005/0203489 | A1 | 9/2005 | Saadat et al. |
| 2005/0251158 | A1 | 11/2005 | Saadat et al. |
| 2006/0200004 | A1 | 9/2006 | Wilk |
| 2006/0241344 | A1 | 10/2006 | Wilk |
| 2006/0241570 | A1 | 10/2006 | Wilk |
| 2007/0032702 | A1 | 2/2007 | Ortiz |
| 2008/0221384 | A1 * | 9/2008 | Chi Sing ............ A61N 5/1015 600/7 |
| 2009/0276055 | A1 | 11/2009 | Harris et al. |
| 2010/0036197 | A1 | 2/2010 | Mesallum |
| 2010/0179417 | A1 | 7/2010 | Russo |
| 2011/0178454 | A1 | 7/2011 | Gagner et al. |
| 2011/0288576 | A1 | 11/2011 | Hoffman |
| 2012/0065469 | A1 * | 3/2012 | Allyn ............ A61B 1/0676 600/109 |
| 2012/0165608 | A1 | 6/2012 | Banik et al. |
| 2012/0184981 | A1 | 7/2012 | Pecor et al. |
| 2012/0239061 | A1 | 9/2012 | Mathur |
| 2013/0165774 | A1 * | 6/2013 | Nocca ............ A61F 5/0083 600/431 |
| 2014/0018722 | A1 | 1/2014 | Scott et al. |
| 2014/0114121 | A1 | 4/2014 | Trivedi |

FOREIGN PATENT DOCUMENTS

| | | |
|---|---|---|
| EP | 2246013 A1 | 11/2010 |
| ES | 2326937 A1 | 10/2009 |
| JP | 3178309 U | 9/2012 |
| WO | 02096327 A2 | 12/2002 |
| WO | 2009097585 A1 | 8/2009 |
| WO | 2012138737 A1 | 10/2012 |
| WO | 2013123235 A1 | 8/2013 |
| WO | 2014062881 A1 | 4/2014 |

OTHER PUBLICATIONS

European Search Report, dated Mar. 24, 2015, corresponding to European Application No. 14192416.7; 7 pages.
Dietel et al., "Endoscopy of Vertical Banded Gastroplasty," The American Surgeon, May 1989, vol. 55; pp. 287-890.
Dietel et al., "Vertical Banded Gastroplasty: Results in 233 Patients," The Canadian Journal of Surgery, Sep. 1986, vol. 29, No. 5; pp. 322-324.
Mason et al., "Vertical Gastroplasty: Evolution of Vertical Banded Gastroplasty,"World Journal of Surgery, Sep. 1998, vol. 22, No. 9; pp. 919-924.
Extended European Search Report dated Sep. 17, 2015, corresponding to European Patent Application 15167339.9; 10 pages.
Extended European Search Report dated Oct. 1, 2015, corresponding to European Application No. 15167342.3; 7 pages.
European Search Report dated Dec. 2, 2015, corresponding to European Application No. 15177233.2; 7 pages.
International Search Report and Written Opinion of hte International Searching Authoirity, dated Jul. 12, 2016, corresponding to International Application No. PCT/US2016/028046; 12 total pages.
European Search Report dated Oct. 4, 2016, corresponding to European Application No. 16178267.7; 7 pages.
European Communicationdated May 26, 2017, corresponding to European Application No. 15167342.3; 4 pages.
European Search Report, dated Mar. 24, 2017, corresponding to European Application No. 16199748.1; 5 pages.
Chinese Office Action dated Feb. 19, 2019 issued in corresponding CN Appln. No. 201510242675.1.

* cited by examiner

ILLUMINATED GASTRIC TUBES AND METHODS OF USE

CROSS-REFERENCE TO RELATED APPLICATION

This application is a divisional application of U.S. patent application Ser. No. 14/276,269, filed on May 13, 2014, the entire contents of which are incorporated by reference herein.

TECHNICAL FIELD

The present disclosure generally relates to surgical instruments, and more particularly, to illuminated gastric tubes used in bariatric procedures.

BACKGROUND

Obesity is reaching epidemic proportions in many regions of the world, particularly in the United States. In order to treat obesity, various bariatric procedures have been developed including, for example, gastric bypass, adjustable gastric banding, and sleeve gastrectomy. The goal in each of these procedures is to reduce the stomach capacity to restrict the amount of food that the patient can eat. The reduced stomach capacity, in turn, results in a feeling of fullness for the patient after ingesting a relatively smaller amount of food. Thus, the patient can achieve significant weight loss.

Sleeve gastrectomy involves transecting a stomach, e.g., using a stapling device or other suitable device, to reduce a stomach volume. Sleeve gastrectomy procedures are often aided by the use of a gastric tube, which serves as a guide or template for transecting the stomach to the appropriate configuration while inhibiting inadvertent transection of stomach or esophageal tissue. Once the stomach has been appropriately transected, the gastric tube is removed and a leak test is performed to determine whether there are any areas of extravasation.

In use, the gastric tube may be advanced into a patient's body through an oral cavity and down through the esophagus into the stomach to provide delineation of the antrum of the stomach, irrigation/suction of fluids, and/or a sizing of a gastric pouch. While being advanced, due at least in part to the circuitous nature of this track, a clinician may need to reposition the gastric tube in various orientations until the gastric tube is properly aligned or bypasses any obstruction(s).

Accordingly, increasing visibility of the gastric tube within a patient's body could aid in navigating the gastric tube to its selected final position within the patient's body and/or reduce the time to perform a desired procedure.

SUMMARY

According to one aspect of the present disclosure, an illuminated gastric tube for use in a bariatric surgical procedure is provided. The illuminated gastric tube includes an elongate tube and an anchor. The elongate tube has a proximal end portion and a distal end portion and defines a lumen along a length thereof. The proximal end portion defines an opening in communication with the lumen.

The elongate tube includes a blunt tip, a light source, and an outer surface. The blunt tip is formed on the distal end portion and is at least partially transparent. The light source is in communication with the blunt tip for illuminating at least the blunt tip. The outer surface extends between the proximal and distal end portions and defines a side opening in communication with the lumen. The side opening is configured and dimensioned for at least one of aspiration and irrigation. The anchor is secured to the elongate tube and is configured to fix the elongate tube within a patient's stomach.

In embodiments, the light source may be housed within the tip. It is further envisioned that the tip includes an inner surface. The light source may be a plurality of light sources that line the inner surface of the tip. The light source may protrude from the inner surface of the tip.

In some embodiments, the gastric tube may include a plurality of depth markings formed along at least a portion of the outer surface.

In some aspects of the present disclosure, the elongate tube may further include an opaque barrier disposed between the proximal and distal end portions to inhibit light emitted by the light source from passing from the tip into the lumen. In further aspects of the present disclosure, the tip may have an arcuate outer surface. The tip may have an opening formed therein configured and dimensioned for at least one of aspiration and irrigation.

In some embodiments, the gastric tube may include a power source supported on the proximal end portion of the elongate tube. The power source may include a battery electrically coupled to the light source.

In further aspects of the present disclosure, the anchor may include an inflatable balloon member.

In embodiments, the elongate tube may further include a movable component attached to the outer surface. The movable component may be movable between an unexpanded position in which the movable component is disposed in abutting engagement with the outer surface and an expanded position in which a distal portion of the movable component bows outwardly from the outer surface of the elongate tube. It is contemplated that the movable component may be slidably coupled to the proximal end portion of the elongate tube and fixedly coupled to the distal end portion of the elongate tube.

In another aspect of the present disclosure, a method of performing bariatric surgery is provided. The method includes providing an illuminated gastric tube. The illuminated gastric tube includes an elongate tube and an anchor. The elongate tube has a proximal end portion and a distal end portion and defines a lumen along a length thereof. The proximal end portion defines an opening in communication with the lumen. The elongate tube includes a blunt tip, a light source, and an outer surface.

The method further includes inserting the gastric tube into an oral cavity of a patient; actuating the light source to illuminate at least the tip; guiding the gastric tube along an enteral pathway; repositioning the gastric tube based on an observed position of the illuminated tip to a selected position within a stomach of a patient; aspirating fluid from a stomach through the side opening of the elongate tube; anchoring the gastric tube to the selected position within a stomach; and transecting a portion of a stomach.

In some aspects of the present disclosure, anchoring the gastric tube may include inflating a balloon supported on the elongate tube with an inflation medium to wedge the balloon between inner surfaces of a stomach. In some embodiments, the balloon may be supported on the distal end portion of the elongate tube. In some embodiments, the method may further include positioning the balloon in an antrum of a stomach.

In further aspects of the present disclosure, guiding the gastric tube along the enteral pathway may include advancing the gastric tube from an oral cavity of a patient through an esophagus of a patient into an antrum of a stomach.

In embodiments, the method may further include moving a movable component supported on the elongate tube from an unexpanded configuration to an expanded configuration in which the movable component bows outwardly from the outer surface of the elongate tube into engagement with a portion of a stomach. In some embodiments, moving the movable component may include sliding the movable component distally relative to the elongate tube.

Other aspects, features, and advantages of the present disclosure will be apparent from the description, the drawings, and the claims.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

As used herein, the term "clinician" refers to a doctor, nurse, or other care provider and may include support personnel. The terms "proximal" or "trailing" each refer to the portion of a structure closer to a clinician, and the terms "distal" or "leading" each refer to a portion of a structure farther from the clinician.

Figure 1:
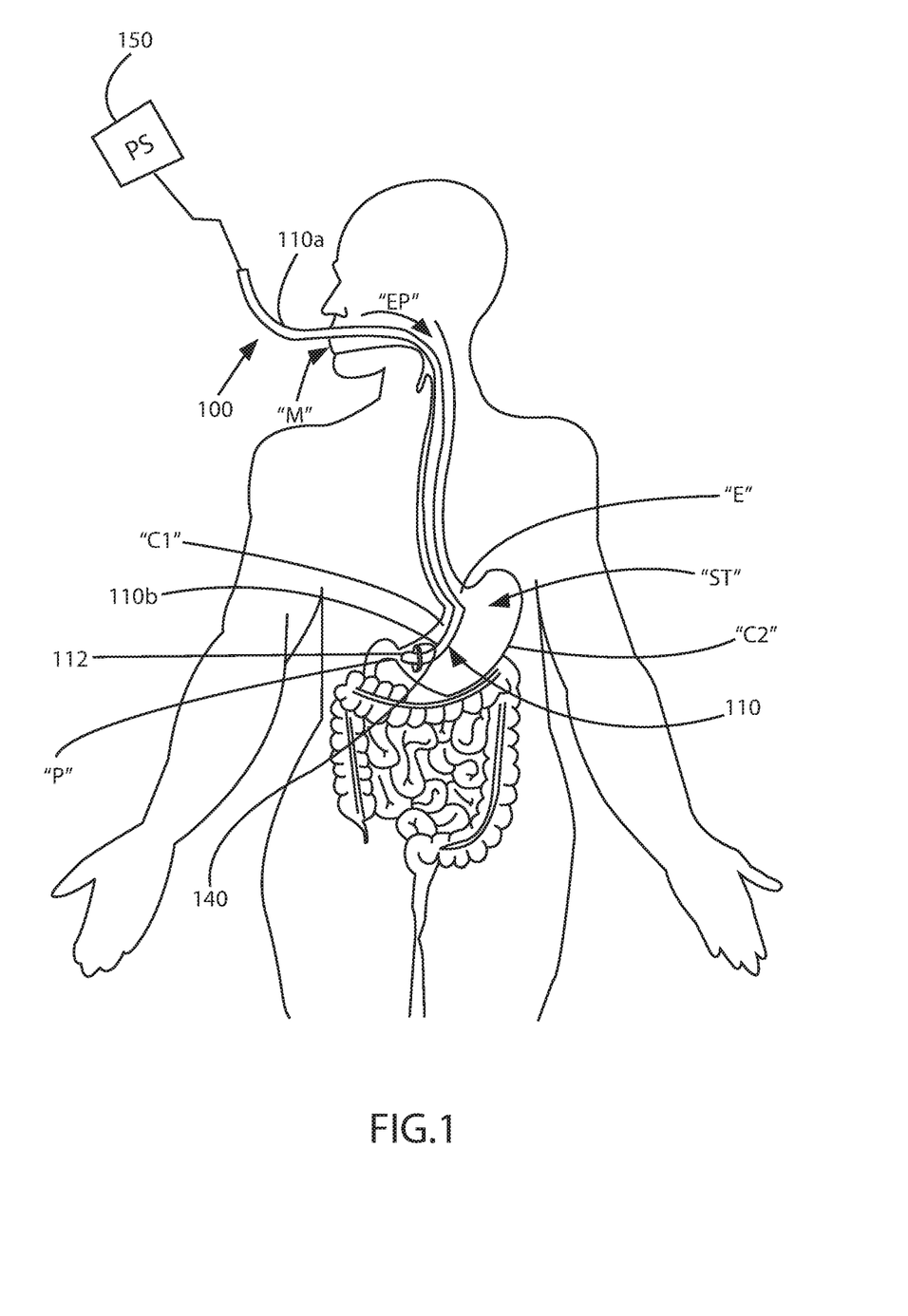
FIG. 1 is a side view of an illustrative embodiment of an illuminated gastric tube being navigated through an enteral pathway of a patient into a stomach of a patient in accordance with the principles of the present disclosure.
Figure 2:
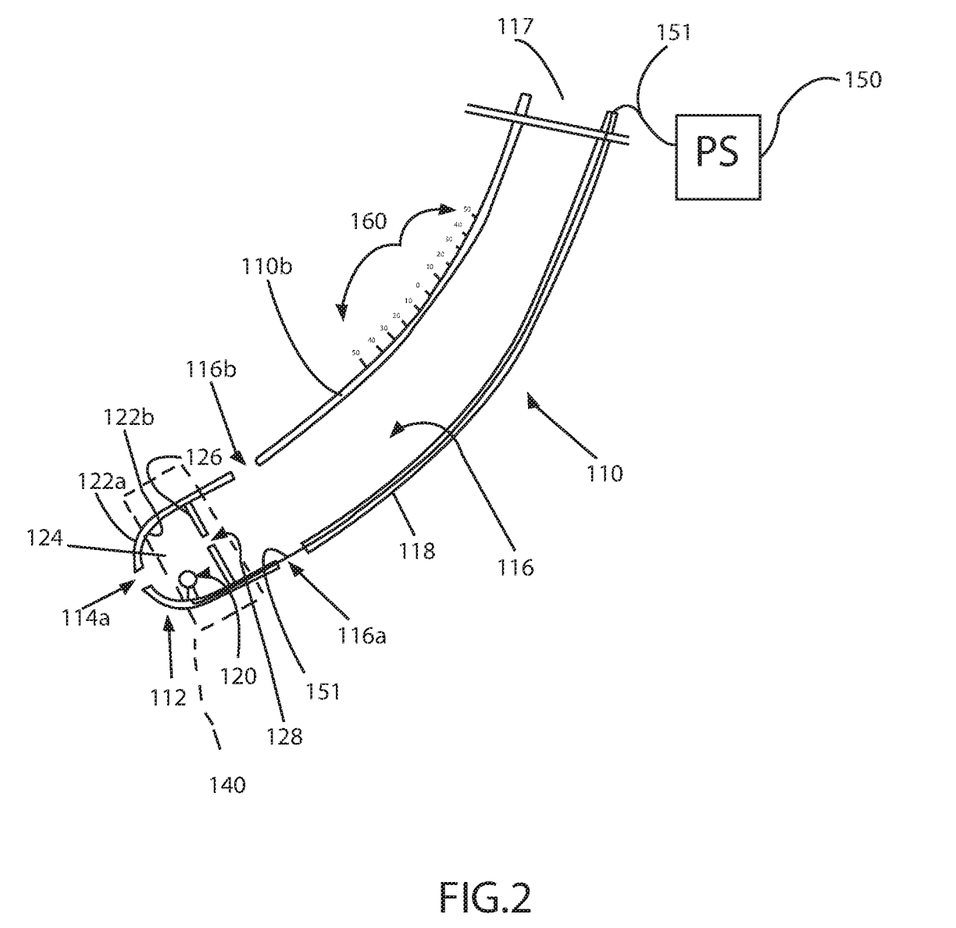
FIG. 2 is a side, cross sectional view, in part phantom, of the gastric tube shown in FIG. 1.
Figure 3:
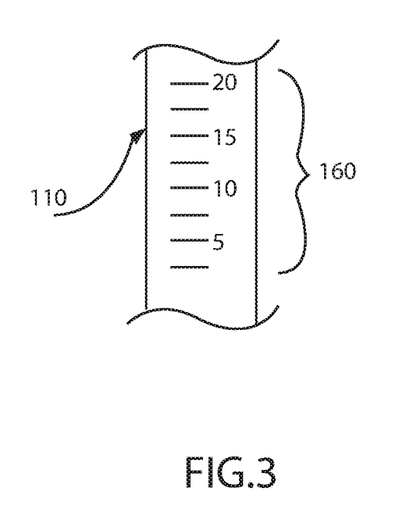
FIG. 3 is an expanded view of depth markings of the gastric tube shown in FIG. 2.

Referring now to FIGS. 1-3, an illuminated gastric tube 100 includes an elongate tube 110 having a light source 120 associated therewith, an anchor, such as, for example, an inflatable balloon member 140 supported on the elongate tube 110, and a power source 150 coupled with the light source 120.

In use, as described in further detail below with reference to FIG. 1, the gastric tube 100 is inserted into an oral cavity (e.g., a mouth "M") of a patient and is advanced distally (e.g., caudally) along an enteral pathway "EP" that includes a track that extends between oral cavity "M" and a stomach "ST" of the patient. The light source 120 illuminates at least a distal tip 112 of the elongate tube 110 so as to aid a clinician in guiding the gastric tube 110 along the enteral pathway "EP." When positioned in the stomach "ST" of the patient (e.g., the antrum or lower part of the stomach), the balloon member 140 can be secured within or fixed to the stomach "ST" by, for example, inflating the balloon member and aid the clinician in performing a bariatric surgical procedure such as a sleeve gastrectomy.

With continued reference to FIGS. 1-3, the elongate tube 110 can be formed of any material with sufficient flexibility to enable the elongate tube 110 to maneuver along the patient's track or enteral pathway "EP" between the oral cavity "M" and the stomach "ST." The elongate tube 110 includes a trailing end portion or proximal end portion 110a and a leading end portion or distal end portion 110b. Elongate tube 110 defines a curved length that extends between the proximal and distal end portions 110a, 110b. It is contemplated that elongate tube 110 can be linear, arcuate, or any shape suitable for a particular bariatric surgical procedure. Elongate tube 110 defines a lumen 116 extending along and through the length of elongate tube 110. The lumen 116 is in fluid communication with side openings 116a, 116b defined in an outer surface 118 adjacent distal end portion 110b.

Figure 4:
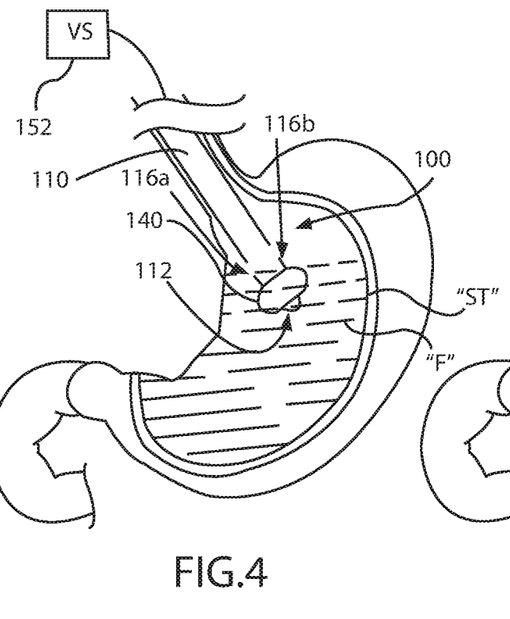
FIGS. 4 and 5 are progressive side views of the gastric tube shown in FIG. 1 aspirating bodily fluid from within a stomach.
Figure 5:
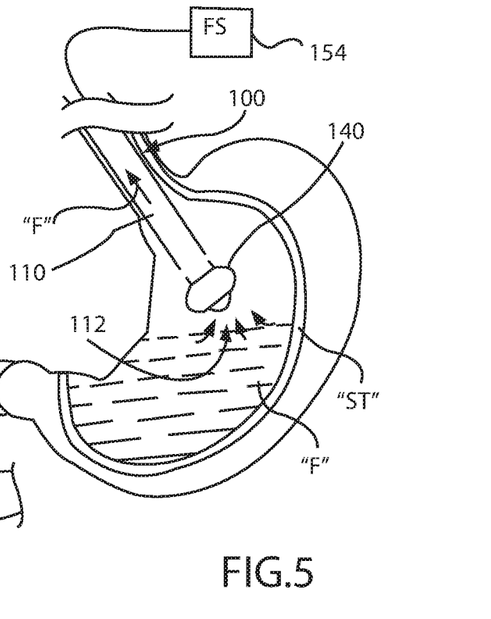

Proximal end portion has an opening 117 configured for connection with a vacuum source 152 (FIG. 4) and/or a fluid source 154 (FIG. 5). Distal end portion 110a includes a distal tip 112. The distal tip 112 can be formed of any material that is solid or substantially solid and transparent or semi-transparent. It is contemplated that the entirety of distal tip 112 may be transparent or semi-transparent or only a portion or portions thereof may be transparent or semi-transparent. The distal tip 112 has a blunt, arcuate outer surface 122a such that penetration of tissue during the advancement of elongate tube 110 through internal body cavities of a patient is resisted and/or prevented. In some embodiments, distal tip 112 can be variously configured, such as, for example, oval, oblong, tapered, uniform, non-uniform, smooth, polished, and/or rounded. Distal tip 112 further includes an arcuate inner surface 122b separated from outer surface 122a by a thickness of distal tip 112. Distal tip 112 defines a distal opening 114a defined in a leading end of the distal tip 112 and extending between inner and outer surfaces 122a, 122b. The side openings 116a, 116b and distal opening 114a together function as an inlet that draws bodily fluids in when lumen 116 is coupled to a vacuum source 152. The vacuum source 152 couples to lumen 116 to aspirate bodily fluids out of a surgical site such as an antrum of a stomach.

Distal tip 112 further includes a light source 120 associated therewith for illuminating at least distal tip 112. Light source 120 may include a plurality of light sources that line, or are distributed on, inner surface 122b of distal tip 112. Light source 120 is housed within distal tip 112 and may protrude from inner surface 122b of distal tip 112 towards an interior cavity 124 of distal tip 112 such that when light source 120 is actuated, light source 120 illuminates the interior cavity 124 of distal tip 112.

Gastric tube 100 further includes a power source 150 in the form of a battery or some other power source to supply power to the light source 120 or plurality of light sources. Power source 150 is electrically coupled to the light source 120 via a wire 151 and is supported on proximal end portion 110a of elongate tube 110. It is contemplated that power source 150 can be a separate component of gastric tube 100. Alternatively, light source 120 may have an internal power source.

Elongate tube 110 may further include an opaque barrier 126 disposed between proximal and distal end portions 110a, 110b of elongate tube 110, and proximal to distal tip 112. Opaque barrier 126 and inner surface 122b of distal tip 112 together define interior cavity 124 of distal tip 112.

Opaque barrier 126 defines a central opening 128 to allow for fluid communication between interior cavity 124 and lumen 116. Opaque barrier 126, however, reduces light loss by inhibiting light emitted from light source 120 from passing from interior cavity 124 of distal tip 112 into lumen 116 or any other portion of gastric tube 100. In this way, upon actuation of light source 120, only distal tip 112 is illuminated such that the precise location of distal tip 112 along the enteral pathway "EP" can be visibly located by a clinician. By being able to precisely locate the distal tip 112, obstructions along the enteral pathway "EP" can be avoided and placement of the distal tip 112 at a selected position within a stomach can be accomplished. In some embodiments, opaque barrier 126 can include a reflective coating.

With reference to FIG. 3, the elongate tube 110 may include one or more depth markings 160 on outer surface 118 of elongate tube 110 that function as an indicator for an insertion depth of the gastric tube 100 along the enteral pathway "EP" of the patient.

Figure 6:
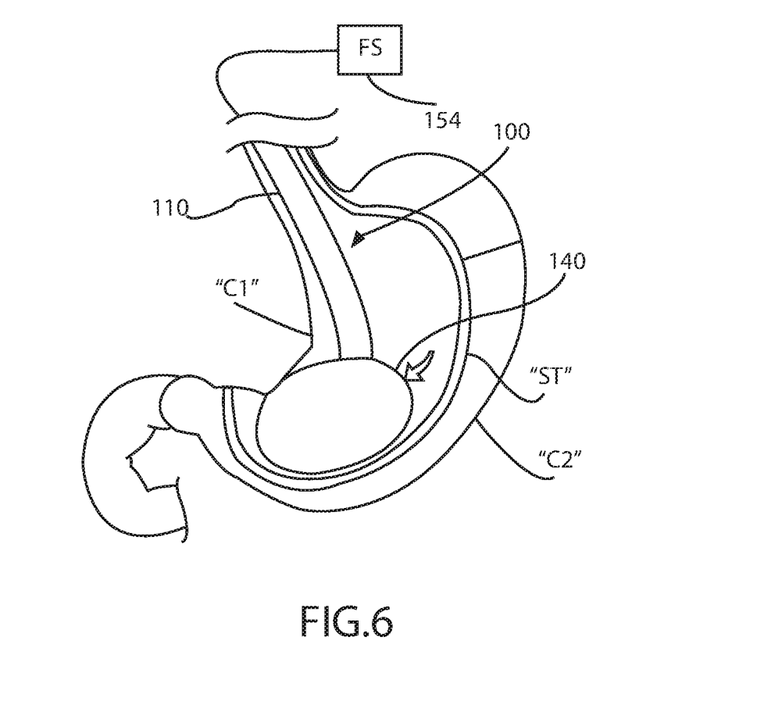
FIG. 6 is a side view of the gastric tube shown in FIG. 1 secured to the stomach.

With reference to FIGS. 4-6, gastric tube 100 may further include an anchor, such as, for example, an inflatable balloon member 140 secured to elongate tube 110. Balloon member 140 is configured to fix elongate tube 110 within a patient's stomach. Balloon member 140 can be in the form of a toroid that is disposed about outer surface 118 of distal end portion 110b such that distal tip 112 protrudes distally from balloon member 140. Balloon member 140 is positioned along outer surface 118 without blocking side openings 116a, 116b. It should be appreciated that, as used herein, the term inflatable balloon member refers to any structure defining a volume that is expandable upon introduction of fluid into the volume, and thus can include a unitary arrangement of material and/or a multi-component arrangement secured together to form, for example, a bladder.

An inflation lumen (not shown) is defined in the elongate tube 110 that is in fluid communication with balloon member 140. The balloon member 140 is adapted to receive inflation fluid (e.g., saline) through the inflation lumen when the inflation lumen is coupled to fluid source 154 adapted to deliver the inflation fluid. Alternatively, and/or additionally, the inflation lumen couples to vacuum source 152 adapted to create a vacuum in the inflation lumen to draw inflation fluid from within the balloon member 140 out of the balloon member 140 to deflate the balloon member 140. As appreciated, the fluid and/or vacuum sources 152, 154 enable a clinician to control the size of the balloon member 140 as desired.

In an exemplary use, as illustrated in FIGS. 4-6, the gastric tube 100 is inserted into a patient, such as, for example, an oral cavity "M" of a patient and is distally advanced toward the stomach "ST" along enteral pathway "EP," which extends from the oral cavity "M," through the esophagus "E," and into the stomach "ST." Light source 120 is actuated by power source 150 to illuminate distal tip 112. With distal tip 112 illuminated, gastric tube 100 is guided along enteral pathway "EP" via observation of the illuminated distal tip 112 with a viewing instrument (not shown). The gastric tube 100 is selectively repositioned based on observed positions of the illuminated distal tip 112 along the enteral pathway "EP." Gastric tube 100 is further guided through the esophagus "E" and selectively positioned within the stomach "ST" of the patient.

Upon positioning the gastric tube 100 within the stomach "ST," the vacuum source 152 functions to aspirate bodily fluid "F" in the stomach "ST." In particular, a vacuum created in the lumen 116 draws the bodily fluid "F" into the distal opening 114a of the distal tip 112 and/or side openings 116a, 116b of elongate tube 110 for proximal extraction of the bodily fluid "F" through lumen 116. As can be appreciated, the vacuum source 152 can also function to collapse the stomach "ST" or portions thereof to facilitate any suitable bariatric procedure such as a sleeve gastrectomy.

As shown in FIG. 6, the fluid source 154 couples to the gastric tube 100 to partially and/or wholly inflate the balloon 140 to anchor the gastric tube 100 within the selected position within the stomach "ST" (e.g., the antrum) and aid the clinician in performing the bariatric surgical procedure. Specifically, as the balloon member 140 is inflated with inflation medium, balloon member 140 is wedged between a first inner surface or a lesser curvature portion "C1" of stomach "ST" and a second inner surface or greater curvature portion "C2" of stomach "ST." With the balloon 140 deflated, a clinician can remove or transect a large portion of the stomach "ST" and staple the remaining portion together. In certain procedures, this is done to limit the size of the patient's stomach "ST" for helping the patient lose weight.

Figure 7:
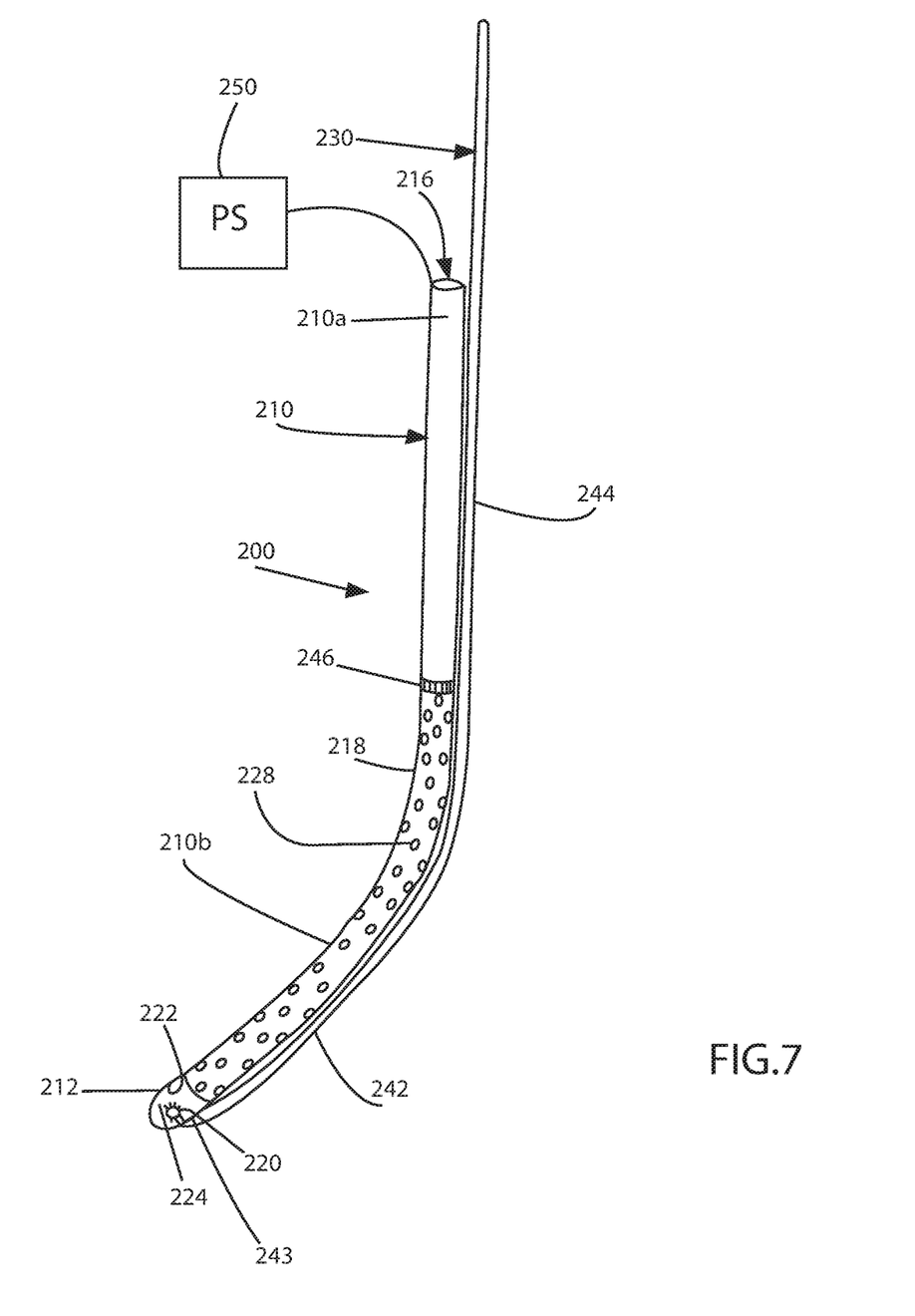
FIG. 7 is a perspective view of another illustrative embodiment of an illuminated gastric tube having a movable component disposed in an unexpanded position in accordance with the principles of the present disclosure.
Figure 8:
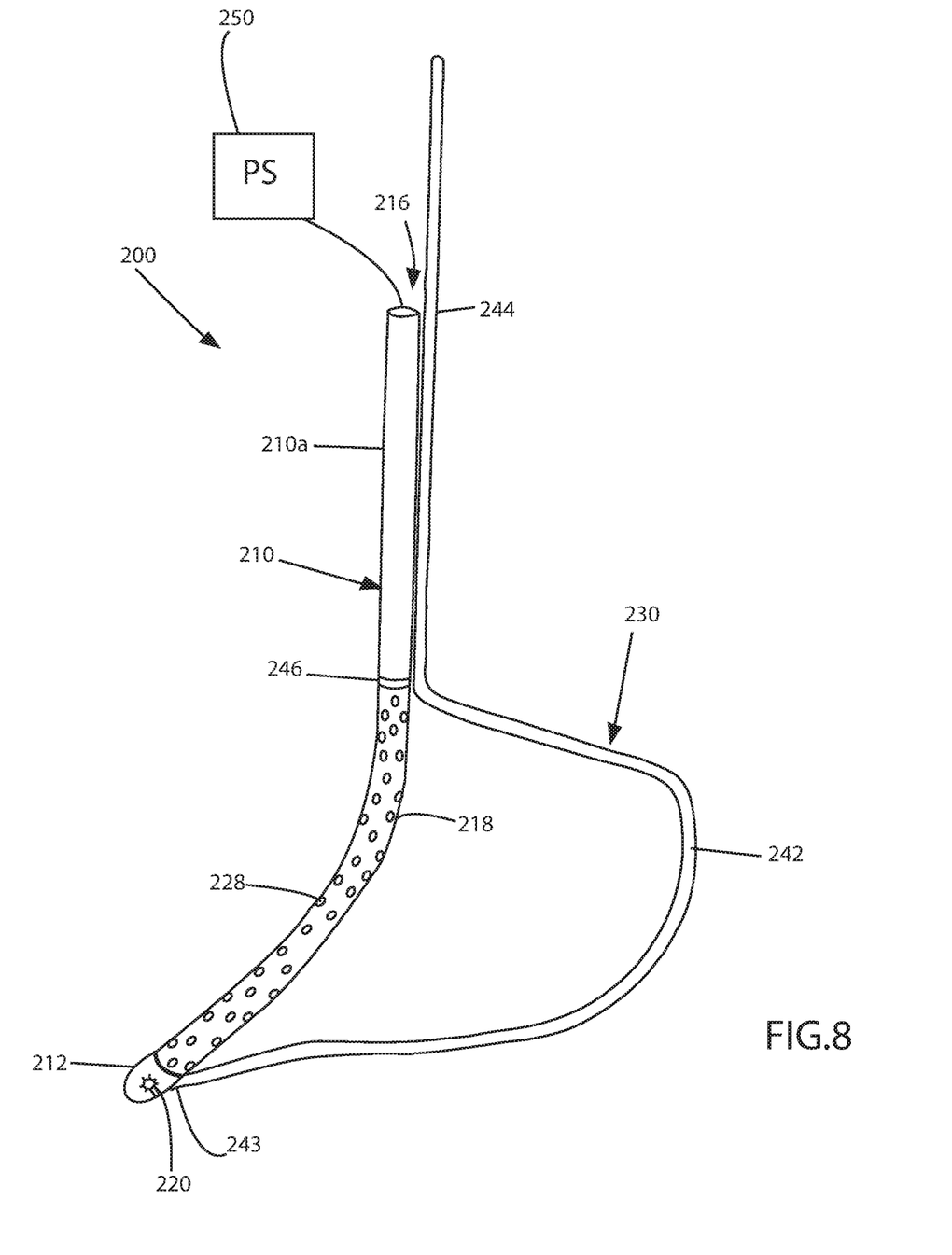
FIG. 8 is perspective view of the gastric tube shown in FIG. 7 with the movable component disposed in an expanded position.

Referring now to FIGS. 7 and 8, another embodiment of an illuminated gastric tube 200, similar to gastric tube 100, is shown. In general, the gastric tube 200 includes an elongate tube 210 having a plurality of openings or apertures 228 and a light source 220 associated with the elongate tube 210, a rod member or movable component 230 coupled to elongate tube 210, and a power source 250, similar to power source 150 discussed above, coupled with the light source 220. In embodiments, the gastric tube 100 described with regard to FIGS. 1-3 may also include movable component 230 translatably or slidably coupled to elongate tube 110 thereof.

The elongate tube 210 includes a trailing end portion or proximal end portion 210a and a leading end portion or distal end portion 210b. Elongate tube 210 defines a curved length that extends between the proximal and distal end portions 210a, 210b. Elongate tube 210 defines a lumen 216 extending along and through the length of elongate tube 210. Elongate tube 210 further includes a plurality of openings or apertures 228 extending between an outer surface 218 and an inner surface (not shown) of elongate tube 210. Apertures 228 provide for fluid communication between lumen 216 and an environment exterior to elongate tube 210. When suction is applied to elongate tube 210, elongate tube 210 can adhere to tissue, such as, for example, stomach tissue, due to the plurality of openings 228 directing suction towards stomach tissue.

Proximal end portion 210a is configured for connection with a vacuum source and/or a fluid source (not shown), similar to vacuum and fluid sources 152, 154 discussed above. Distal end portion 210b includes a distal tip 212, similar to distal tip 112 discussed above. Distal tip 212 includes a light source 220 associated therewith for illuminating at least distal tip 212. Light source 220 may include a plurality of light sources that line, or are distributed on, an inner surface 222 of distal tip 212. Light source 220 is housed within distal tip 212 and may protrude from inner surface 222 of distal tip 212 towards an interior cavity 224 of distal tip 212 such that when light source is actuated, light source illuminates the interior cavity 224 of distal tip 212. In any of the embodiments disclosed herein, a light source can be included in the tip of the tube device, distributed along its length, or in other configurations.

Gastric tube 200 includes a movable component 230 coupled to elongate tube 210. Movable component 230 is formed from a semi-rigid, resiliently flexible material, e.g., a suitable elastomer, and defines a length greater than the length of elongate tube 210 such that movable component 230 can be accessed outside the patient and/or remotely of the surgical site. Movable component 230 defines a distal portion 242 having a distal end 243 and a proximal portion 244. Distal end 243 of movable component 230 is integrally, i.e., monolithically, formed with or otherwise affixed to distal tip 212. A coupling 246, e.g., a ring, sleeve, hook, latch, etc., affixed to elongate tube 210 slidably receives a portion of movable component 230 therethrough to slidably couple movable component 230 to elongate tube 210 intermediate the distal and proximal end portions 210a, 210b of elongate tube 210.

As a result of the above-configuration, movable component 230 is slidable through coupling 246 and relative to elongate tube 210 between an unexpanded or contracted position and an expanded or deployed position. The unexpanded position corresponds to a first condition of gastric tube 200, as shown in FIG. 7, wherein distal portion 242 of movable component 230 extends along and is in abutting engagement with the outer surface 218 of elongate tube 210 and is in substantially parallel relation relative thereto. The expanded position corresponds to a second condition of gastric tube 200, as shown in FIG. 8, wherein distal portion 242 of movable component 230 is bowed outwardly from elongate tube 210 and is spaced therefrom. In the expanded position, movable component 230 defines a configuration that generally complements the curvature of a greater curvature portion of a stomach (FIG. 6).

Proximal portion 244 of movable component 230 may be grasped and manipulated relative to elongate tube 210 to transition movable component 230 between the unexpanded and expanded positions. As mentioned above, movable component 230 is dimensioned such that proximal portion 244 is accessible from outside the patient, thus readily enabling manipulation thereof. More specifically, translating movable component 230 distally relative to elongate tube 210 and coupling 246 urges movable component 230 distally through coupling 246 such that distal portion 242 of movable component 230 is bowed outwardly relative to elongate tube 210 towards the expanded position. Translating movable component 230 proximally relative to elongate tube 210 pulls movable component 230 proximally through coupling 246 such the distal portion 242 of movable component 230 is pulled inwardly relative to elongate tube 210 towards the unexpanded position.

Tube 200 may be used in a similar manner as tube 100. In an exemplary use, with movable component 230 in the unexpanded position, the gastric tube 200 is inserted into a patient, such as, for example, an oral cavity of a patient and is distally advanced toward a stomach of the patient along an enteral pathway that extends from the oral cavity, through an esophagus of the patient, and into the stomach, as described above with regard to FIGS. 1 and 4-6. Light source 220 is actuated by power source 250 to illuminate distal tip 212. With distal tip 212 illuminated, gastric tube 200 is guided along the enteral pathway via observation of the illuminated distal tip 212. The gastric tube 200 is selectively repositioned based on observed positions of the illuminated distal tip 212 along the enteral pathway. Gastric tube 200 is further guided through the esophagus and selectively positioned within the stomach of the patient.

Upon positioning the gastric tube 200 within the stomach, proximal portion 244 of movable component 230 is translated distally relative to elongate tube 210 such that distal portion 242 of movable component 230 bows outwardly relative to elongate tube 210 towards the expanded position. As distal portion 242 of movable component 230 bows outwardly towards the expanded position, elongate tube 210 is urged towards and into complementary mating relation with the lesser curvature portion of the stomach, while distal portion 242 of movable component 230 is urged towards and into complementary mating relation with the greater curvature portion of the stomach. As such, the orientation of gastric tube 200 with elongate tube 210 extending along the lesser curvature portion of the stomach between the esophageal sphincter and the pyloric sphincter can be readily achieved. As a result of this configuration of gastric tube 200 in the expanded position, the above-described orientation of gastric tube 200 within the stomach is maintained despite spasms, folding, spiraling, and/or shifting of the stomach.

Once the proper orientation of elongate tube 210 has been achieved, suction is applied within lumen 216 for suctioning any remaining contents within the stomach into lumen 216 of elongate tube 210 through apertures 228. Application of suction within lumen 216 also suctions the lesser curvature portion of the stomach to the outer surface or periphery 218 of elongate tube 210, to ensure and maintain the complementary mating relation of elongate tube 210 with the lesser curvature portion of the stomach.

With elongate tube 210 maintained in position relative to the lesser curvature portion of the stomach as a result of the applied suction, proximal portion 244 of movable component 230 is translated proximally relative to elongate tube 210 such that the distal portion 242 of movable component 230 is pulled inwardly relative to elongate tube 210 back to the unexpanded position. As suction is maintained at this point, elongate tube 210 is maintained in the position detailed above despite contraction of distal portion 242 of movable component 230.

Once distal portion 242 of movable component 230 has been returned to the unexpanded position, transection of the stomach adjacent elongate tube 210 on an opposite side of elongate tube 210 relative to the lesser curvature portion of the stomach may be effected in any suitable fashion, e.g., using a stapling device or other suitable device. Transection in this manner reforms the stomach to a tubular-shaped configuration that generally approximates the outer dimension of elongate tube 210 and extends between the esophageal sphincter and the pyloric sphincter. As can be appreciated, the diameter of elongate tube 210 may be selected in accordance with a desired diameter of the tubular-shape reformed stomach.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described herein, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:
1. A gastric tube for use in a bariatric surgical procedure, the gastric tube comprising:
   an elongate tube having a proximal end portion and a distal end portion, the elongate tube defining a lumen along a length thereof, the proximal end portion defining an opening in communication with the lumen, the elongate tube including:
  a blunt tip formed on the distal end portion and being at least partially transparent;
  a light source in communication with the blunt tip for illuminating at least the blunt tip; and
  an outer surface that extends between the proximal and distal end portions and defines a side opening in communication with the lumen, the side opening configured and dimensioned for at least one of aspiration and irrigation;
  an opaque barrier extending across an interior of the elongate tube and being configured to inhibit light emitted by the light source from passing from the blunt tip into the lumen; and
an anchor secured to the elongate tube and configured to fix the elongate tube within a patient's stomach.

2. The gastric tube as recited in claim 1, wherein the light source is housed within the blunt tip.

3. The gastric tube as recited in claim 1, wherein the blunt tip includes an inner surface, wherein the light source is a plurality of light sources disposed along the inner surface of the blunt tip.

4. The gastric tube as recited in claim 1, further including a plurality of depth markings formed along at least a portion of the outer surface.

5. The gastric tube as recited in claim 1, wherein the blunt tip includes an inner surface, wherein the light source protrudes from the inner surface of the blunt tip.

6. The gastric tube as recited in claim 1, wherein the blunt tip has an arcuate outer surface.

7. The gastric tube as recited in claim 1, wherein the blunt tip defines an opening formed therein configured and dimensioned for at least one of aspiration and irrigation.

8. The gastric tube as recited in claim 1, further including a power source coupled with the light source for supplying power to the light source, wherein the power source is supported on the proximal end portion of the elongate tube.

9. The gastric tube as recited in claim 8, wherein the power source includes a battery electrically coupled to the light source.

10. The gastric tube as recited in claim 1, wherein the anchor includes an inflatable balloon member.

11. The gastric tube as recited in claim 1, further including a movable component attached to the outer surface, the movable component including a distal portion, the movable component being movable between an unexpanded position in which the movable component is disposed in abutting engagement with the outer surface and an expanded position in which the distal portion of the movable component bows outwardly from the outer surface of the elongate tube.

12. The gastric tube as recited in claim 11, wherein the movable component is slidably coupled to the proximal end portion of the elongate tube and fixedly coupled to the distal end portion of the elongate tube.

13. A gastric tube for use in a bariatric surgical procedure, the gastric tube comprising:
  an elongate tube defining a longitudinally-extending lumen and having a transparent, blunt distal tip;
  a light source disposed within the distal tip for illuminating the distal tip; and
  an opaque barrier extending across an interior of the elongate tube and being configured to inhibit light emitted by the light source from passing from the distal tip into the lumen.

14. The gastric tube as recited in claim 13, wherein the elongate tube has an outer surface that extends between a proximal end portion and a distal end portion thereof, the outer surface defining a side opening in communication with the lumen, the side opening configured for at least one of aspiration and irrigation.

15. The gastric tube as recited in claim 13, further including an anchor secured to the elongate tube and configured to fix the elongate tube within a patient's stomach.

16. The gastric tube as recited in claim 13, wherein the distal tip includes an inner surface and the light source protrudes from the inner surface of the distal tip.

17. The gastric tube as recited in claim 13, wherein the distal tip defines an opening configured for at least one of aspiration and irrigation.

18. The gastric tube as recited in claim 13, further including a power source coupled to the light source for supplying power to the light source.

19. The gastric tube as recited in claim 13, further including a movable component coupled to the elongate tube, the movable component configured to move between an unexpanded position in which the movable component is disposed in abutting engagement with an outer surface of the elongate tube, and an expanded position in which a distal portion of the movable component bows outwardly from the outer surface of the elongate tube.

* * * * *